(12) United States Patent
Lopez (10) Patent No.: US 9,872,760 B2
(45) Date of Patent: Jan. 23, 2018

(54) SOFT TISSUE TENSIONING AND FIXATION DEVICE

(71) Applicant: Mandi J. Lopez, Baton Rouge, LA (US)

(72) Inventor: Mandi J. Lopez, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 15/093,469

(22) Filed: Apr. 7, 2016

(65) Prior Publication Data

US 2016/0296319 A1    Oct. 13, 2016

Related U.S. Application Data

(60) Provisional application No. 62/145,552, filed on Apr. 10, 2015.

(51) Int. Cl.
*A61F 2/08* (2006.01)
*A61B 17/04* (2006.01)

(52) U.S. Cl.
CPC ............... *A61F 2/08* (2013.01); *A61B 17/04* (2013.01); *A61F 2/0811* (2013.01);
(Continued)

(58) Field of Classification Search
CPC  A61F 2/08; A61F 2/20811; A61F 2002/0817; A61F 2002/0823; A61F 2002/0864
(Continued)

(56) References Cited

U.S. PATENT DOCUMENTS

| | | | |
|---|---|---|---|
| 5,108,433 A | 4/1992 | May et al. | 623/13.13 |
| 5,562,668 A | 8/1996 | Johnson | 623/13.13 |

(Continued)

OTHER PUBLICATIONS

Bodó et al., "Development of a tension-adjustable implant for anterior cruciate ligament reconstruction," Joint Diseasess and Related Surgery, vol. 19, No. 1, pp. 27-32 (2008).

(Continued)

*Primary Examiner* — David Isabella
*Assistant Examiner* — Suba Ganesan
(74) *Attorney, Agent, or Firm* — John H. Runnels (57) ABSTRACT

An improved device provides a cost-effective, time-effective way to stably and reliably affix soft tissues (e.g., tendon or ligament) to the surface of anatomical structures with comparable or greater strength and stiffness (e.g., bone). The device does not require specialized procedures or tools. A single device applies both incremental tensioning and compression to the soft tissue being affixed. The device allows the user, typically a physician or veterinarian, to reliably manipulate, control, and maintain tissue tension. The device is versatile, and can accommodate attachment of soft tissues of different sizes and mechanical properties to bone or to other soft tissues. These features provide flexibility to human and veterinary health practitioners in a variety of specialized areas including orthopedics, joint stabilization, soft tissue repair, spinal surgery, and plastic surgery.

11 Claims, 7 Drawing Sheets

(52) U.S. Cl.
CPC ......... *A61F 2002/0817* (2013.01); *A61F 2002/0823* (2013.01); *A61F 2002/0829* (2013.01); *A61F 2002/0888* (2013.01); *A61F 2210/0004* (2013.01); *A61F 2220/0008* (2013.01); *A61F 2250/0012* (2013.01)

(58) Field of Classification Search
USPC ..................................................... 623/13.13
See application file for complete search history.

(56) References Cited

U.S. PATENT DOCUMENTS

| | | | | |
|---|---|---|---|---|
| 6,235,058 | B1* | 5/2001 | Huene | A61F 2/08 606/151 |
| 6,544,281 | B2 | 4/2003 | ElAttrache et al. | 606/232 |
| 8,540,734 | B2 | 9/2013 | Hoof | 606/144 |
| 9,044,315 | B2 | 6/2015 | Lopez et al. | 606/151 |
| 2011/0112640 | A1 | 5/2011 | Amis et al. | 623/13.14 |

OTHER PUBLICATIONS

Borne et al., "Novel anterior cruciate ligament graft fixation device reduces slippage," Med Devices (Auckland), 6:59-68, 2013. doi: dx.doi.org/10.2147/MDER.S43802.

Lopez et al., "Biomechanical characteristics of an implant used to secure semitendinosus-gracilis tendon grafts in a canine model of extra-articular anterior cruciate ligament reconstruction," Vet Surg., 29:599-604, 2007.

Lopez et al., Initial femoral fixation properties of one novel and two established devices in canine cranial cruciate ligament reconstruction, proceedings American College of Veterinary Surgeons Annual Symposium E15, 2006. (Abstract).

Lopez et al., Initial femoral fixation properties of one novel and two established devices in canine cranial cruciate ligament reconstruction, 41st American College of Veterinary Surgeons Annual Symposium Washington DC, Oct. 4-7, 2006. (Poster).

Lopez et al., Initial femoral fixation properties of one novel and two established devices in canine cranial cruciate ligament reconstruction, Phi Zeta Research Day, LSU SVM, Baton Rouge, LA, Sep. 27, 2006. (Poster).

Lopez et al., "In vivo application of novel and commercially available bioabsorbable implants for tibial fixation of cranial cruciate ligament reconstruction grafts," 45th American College of Veterinary Surgeons Meeting, Chicago, IL, Nov. 5, 2011. (Presentation).

* cited by examiner

Fig. 3F

SOFT TISSUE TENSIONING AND FIXATION DEVICE

PRIORITY CLAIM

The benefit of the 10 Apr. 2015 filing date of U.S. provisional patent application Ser. No. 62/145,552 is claimed under 35 U.S.C. §119(e) in the United States, and is claimed under applicable treaties and conventions in all countries. The complete disclosure of the priority application is hereby incorporated by reference in its entirety.

TECHNICAL FIELD

This invention pertains to apparatus and methods to affix soft tissue to bone or to other tissue, useful for example in anterior cruciate ligament (ACL) or cranial cruciate ligament (CCL) reconstruction grafts.

BACKGROUND ART

Surgical procedures, both human and veterinary, often require the fixation of soft tissue. One common example is anterior cruciate ligament (ACL) reconstruction. ACL reconstruction exemplifies the problems often associated with surgical fixation. A significant fraction of patients—as high as 40%—experience unsatisfactory outcomes caused by tension loss during implantation, or by post-operative cyclical loading. It is important for the surgeon to be able to accurately estimate and maintain tissue tension and stability. However, the surgeon's ability to estimate and maintain tissue tension can be compromised by implants whose installation requires multiple steps. During the fixation procedure, many conventional devices provide inconsistent tissue tensioning, and a loss of tension often results. Post-operative slippage at the fixation site also contributes to the problem. The holding strength of many conventional devices is insufficient to prevent tissue slippage during the initial post-operative period. Current standards for post-operative rehabilitation call for strong initial fixation. However, it is difficult if not impossible for many conventional devices to achieve sufficiently strong fixation.

Conventional technologies for the fixation of soft tissues (e.g., tendon) to anatomical structures with comparable or greater strength and stiffness (e.g., bone) has relied primarily on variations of traditional hardware devices such as screws, washers, staples, pins, and the like. Such conventional devices are ineffective at maintaining tissue tension during tissue fixation. Nor do they permit incremental and stable adjustments to tissue tensioning during the process. Conventional devices often require a patient to undergo multiple procedures, procedures that are often specific to the particular device employed, that are usually extraneous to the primary surgical procedure, and that would otherwise be unnecessary. Where bone tunnels are used, conventional devices are often located some distance from the tunnel. A substantial disadvantage of nearly all prior devices is that they do a poor job of maintaining the proper tension while the soft tissue is secured. No previous device known to the inventor permits the convenient, incremental, reversible, securely-maintained application of tissue tension during the affixing process.

Limitations of many conventional devices include: the time required for installation; otherwise extraneous procedures needed for device installation; unreliable tissue holding strength; loss of tissue tension during the affixing procedure; and the expense of acquiring and maintaining specialized application equipment that often has no other use.

Amis et al., patent application publication no. US 2011/0112640 discloses a graft fixation device for fixing a ligament graft to a bone. The device comprises a locating means for locating the device in the bone and a graft support means arranged to support the graft, wherein the graft support means allows adjustment of the position of the graft relative to the bone. The graft support means may be rotated to provide adjustment. Alternatively the graft support means may be arranged to slide axially or to move radially to provide adjustment.

May et al., U.S. Pat. No. 5,108,433 discloses a prosthetic device for replacing a ligament or tendon. An adjustable connector allows tension on the ligament to be increased or decreased. Three embodiments of the adjustable connector are described: one employs a pin with a threaded shaft and a cylinder with a threaded bore, one employs a ratchet plate and a spool, and one employs cleats.

Johnson, U.S. Pat. No. 5,562,668 describes a screw tensioning device for holding one end of a ligament graft.

ElAttrache et al., U.S. Pat. No. 6,544,281 discloses a method for securing soft tissue to bone. A blind hole or socket is created in the bone at the location the graft is to be secured. Preferably, suture is then passed through the graft at desired points. A cannulated driver is pre-loaded with a cannulated plug or screw slidably disposed onto the distal portion of the driver. The driver is inserted into the hole with the screw or plug just outside the hole. Tension is then placed on the suture. Once adequate tension is achieved on the suture, the driver is pressed into the hole, which engages the first thread or bump of the screw or plug on the bone. The screw or plug is then fully advanced into the hole using the driver.

Lopez and Monroe, U.S. Pat. No. 8,603,115 discloses a soft tissue fixation device for use in ACL or CCL reconstruction. A base member has a passageway extending perpendicularly from the top surface through the bottom surface. The passageway is sized to allow soft tissue to be inserted through it. An affixing member is attachable to the base member. The base member has a notched section in the top surface extending from the passageway to a first perimeter section of the base member sized to accommodate at least a portion of the graft. The base member is secured to bone. The base member is also provided with a sleeve whose interior wall surfaces form a part of the passageway and is sized to be inserted into the bone opening. The affixing member is provided with a series of teeth members extending downward from its lower surface. The teeth members are positioned so that when the affixing member is attached to the base member the teeth members will extend across and into the notched section of the top surface of the base member. The opposite ends of the affixing member are shaped to fit into aligned notches positioned along perimeter sections of the base member bottom surface for attaching the clip member to the base member.

See also: Lopez M J, Monroe W T. Initial Femoral Fixation Properties of One Novel and Two Established Devices in Canine Cranial Cruciate Ligament Reconstruction, Proceedings American College of Veterinary Surgeons Annual Symposium E15, 2006. (Abstract); Lopez M J, Borne A, Monroe W T, Bommala P, Kelly L, Zhang N. Novel anterior cruciate ligament graft fixation device reduces slippage. Med Devices (Auckland) 6:59-68, 2013; Lopez M J, Casey J P, Spencer N D, Monroe W T. Initial femoral fixation properties of one novel and two established devices in canine cranial cruciate ligament reconstruction. 41st American College of Veterinary Surgeons Annual Symposium, Washington D.C., Oct. 4-7, 2006 (Poster); Lopez M J, Casey J P, Spencer N D, Monroe W T. Biomechanical characteristics of an implant used to secure semitendinosus-gracilis grafts in a canine model of extra-articular anterior cruciate ligament reconstruction. Vet Surg 36:599-604, 2007; Lopez M J et al., "In vivo application of novel and commercially available bioabsorbable implants for tibial fixation of cranial cruciate ligament reconstruction grafts". 45th American College of Veterinary Surgeons Meeting, Chicago, Ill., Nov. 5, 2011. (Presentation)

Hoof, U.S. Pat. No. 8,540,734 discloses an adjustable, stand-alone tensioning system that allows an operator to provide adjustable tension to a suture during surgery, using a spring mechanism. The device is evidently designed to be used as a tool during surgery, but not to be implanted and to remain in a patient after surgery. The device is evidently designed to apply tension to a suture, rather than directly to a graft tissue.

L. Bodó et al., "Development of a tension-adjustable implant for anterior cruciate ligament reconstruction," Joint Dis. Rel. Surg., vol. 19, pp. 27-32 (2008) discloses a "loop-in-loop" technique for anterior cruciate ligament reconstruction. The implant contains two parts: a plastic strap with a smooth inner surface and a serrated outside surface; and a plastic ring with a serrated latch. The two serrated surfaces of the two parts allow one-way movement of the plastic strap in the ring to adjust tightening of the graft.

DISCLOSURE OF THE INVENTION

I have discovered an improved device that provides a cost-effective, time-effective way to stably and reliably affix soft tissues (e.g., tendon or ligament) to the surface of anatomical structures having greater or comparable strength and stiffness (e.g., bone). The novel "GrabTen™" device does not require specialized procedures or tools. A single device applies both incremental tensioning and compression to the soft tissue being affixed. The GrabTen™ device allows the user, typically a physician or veterinarian, to reliably manipulate, control, and maintain tissue tension. The device is versatile, and can accommodate different soft tissue types and different hard tissue types. These features provide flexibility to human and veterinary health practitioners in a variety of specialized areas including orthopedics, joint stabilization, soft tissue repair, spinal surgery, and cosmetic or reconstructive surgery.

The novel device is an affixing device with adjustable tensioning capability. It may be used in joint stabilization procedures (e.g., hip, shoulder, elbow, knee). It also has various applications in plastic surgery and soft tissue reconstruction. The novel device is also useful for soft tissue repair procedures, such as repairing tendon and ligament ruptures or detachments. The device is versatile and can accommodate multiple types of tissues affixed to multiple types of surfaces. The novel device requires no spring mechanism. The device preferably applies tension directly to the graft; it is also feasible to apply tension to a suture, where the suture is in turn attached to the tendon or other soft tissue.

The novel device allows single-handed, incremental tissue tensioning, followed by fixation. No specialized procedures or equipment are required to install the "GrabTen™" device. The device allows the user to manipulate and maintain tissue tension reliably. The device permits the surgeon to "dial a tension." That is, the surgeon pulls the graft to the desired macro or gross level of tension. The surgeon then reversibly secures the graft to the top portion of the device, and makes fine adjustment to the tension by rotating the device's cap, which advances the graft further through the bone tunnel. At each "click" or incremental step the tension is maintained by the device itself until the desired fine tuning is reached, at which point the device is secured in place, e.g., by snapping the cap onto the base.

The device is designed to sit over a bone tunnel or other tissue surface at or near the site of soft tissue fixation.

The device may be installed rapidly and efficiently; it does not inherently require any subsequent procedures following the initial installation (as do many prior devices). It maintains tension on the tissue reliably both during the affixing procedure and post-operatively. It does not inherently require the use of any specialized equipment, beyond standard surgical tools.

MODES FOR CARRYING OUT THE INVENTION

Figures 1A, 1B, 1C:
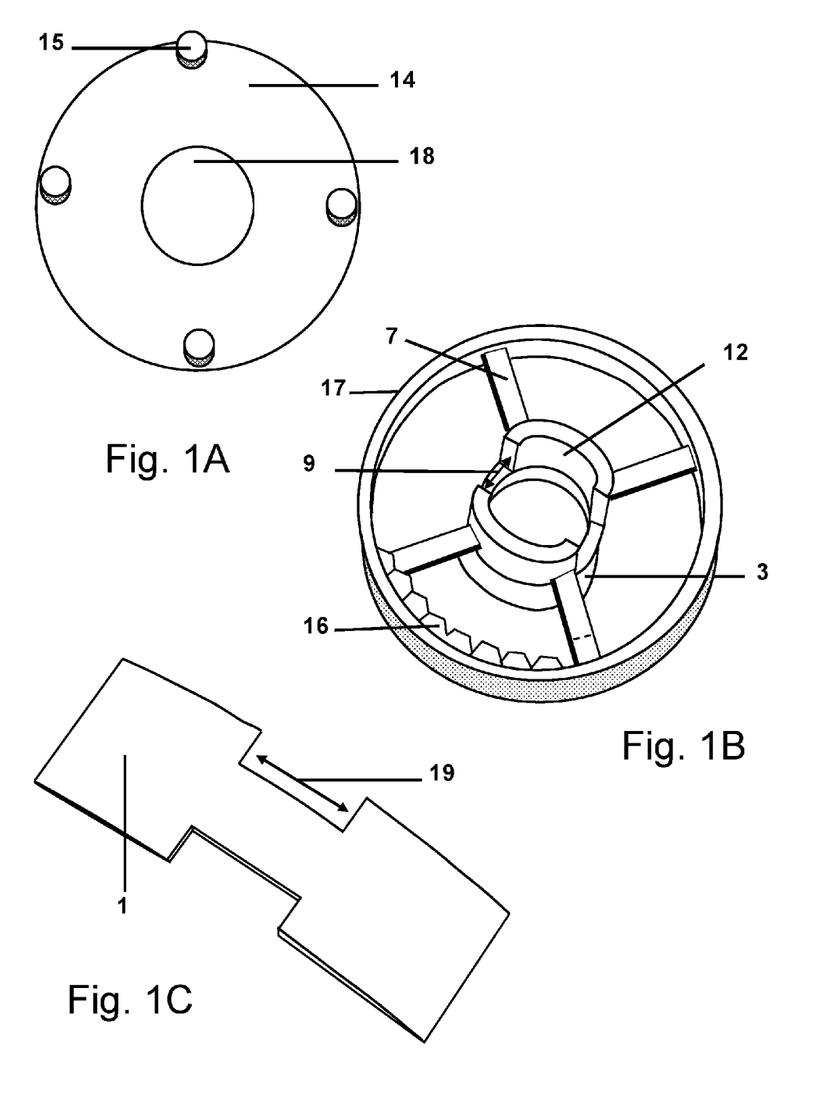
FIGS. 1A-C depict a three-component embodiment of the invention.

One embodiment of the novel device, depicted in FIGS. 1A, 1B, and 1C, comprises three principal components: a base 3, a movable disc 14 capable of rotating within the perimeter wall 17 of base 3 for tissue tensioning, and affixing component 1. The graft tissue passes into hollow sleeve 12 within base 3, and then through notch 9. In this embodiment, the base comprises two concentric circular features when viewed from "above." (Throughout the specification and claims, unless context clearly indicates otherwise, it should be understood that directional terms such as "above," "vertical," the "z-axis," "top," "bottom," and the like should be interpreted as being wholly or partly arbitrary. Such directional terms are used for convenience. They should be understood as having meaning relative to other directional terms—for example, the "top" direction is opposite the "bottom" direction. These terms should not be interpreted as referring to absolute directions (e.g., up or down relative to gravity) unless context clearly indicates otherwise.)

The long axis of hollow sleeve 12 is centered on the z-axis. At or near its vertical midpoint, the outer surface of hollow sleeve 12 is attached to perimeter wall 17 by connecting spokes 7, for example four such spokes 7, whose long axes are parallel to the xy-plane. Spokes 7 attach to hollow sleeve 12 at or near the midpoint of the length of sleeve 12. The central axis of sleeve 12 coincides with the central axis of perimeter wall 17, the "z-axis." In use, sleeve 12 extends along the negative z-axis (e.g., below base 3 and into a bone tunnel). The outer surface of central sleeve 12 preferably includes a series of threads, ledges, or ridges (not shown) to interdigitate with or impart friction to the interior surface of the bone tunnel, to resist pulling out and to resist rotation. Sleeve 12 also extends along the positive z-axis (above the bone surface), above the top surface of spokes 7. The bottom surfaces of spokes 7 are designed to lie upon the bone surface. The bottom surfaces of spokes 7 preferably include spikes or wedges (not shown) to assist in securing them to the bone surface. Along the positive z-axis central sleeve 12 has two openings 9 opposite one another. (Other embodiments have a single opening 9 in sleeve 12. A single opening is preferred as sleeve 12 then possesses greater structural integrity.) Within perimeter wall 17, just above the level of spokes 7, is a series of teeth 16, preferably identical and equally spaced, that extend a short distance into the space between wall 17 and sleeve 12. Wall 17 extends in the positive z-direction approximately half the distance that sleeve 12 extends in the positive z-direction (i.e., the distance above the bone surface when the device is in place). Disc 14 has a central hole 18 sized to accommodate sleeve 12. Disc 14 is sized to fit into the space between sleeve 12 and wall 17. On the outer edge of disc 14 is a series of pegs 15 that extend in the positive z-direction from the surface of disc 14 to approximately half the height of central sleeve 12. Pegs 15 reversibly interdigitate with teeth 16 on wall 17, such that disc 14 can be held in place by the interdigitation of teeth 16 and pegs 15 as disc 14 rotates in either a clockwise or a counter-clockwise direction around central sleeve 12. The graft, or a suture attached to the graft, can be affixed to pegs 15 to allow incremental graft tensioning. (In many cases there is no need for a suture. Without any suture, depending on the embodiment, the graft can be gripped by forceps along with the affixing member, or the graft can be looped over pegs or the like on the affixing member or movable disc.) Affixing member 1 preferably has an arched shape with a narrow central portion 19 and wider edges. Beveled edges, steps, or ledges (not shown) on the central portion 19 fit between and interdigitate with beveled edges, steps, or ledges (not shown) on openings 9 on the portion of central sleeve 12 that extends away from the bone (in the direction of the positive z-axis). Openings 9 allow the graft tissue to pass through. The broad ends of affixing component 1 interdigitate with the outer surface of perimeter wall 17, which preferably also has a series of beveled edges, steps, or ledges (not shown). Thus the distance between affixing member 1 and base 3 is adjustable at both the central and the peripheral aspects.

The graft is incrementally tightened by rotating disc 14. When the desired tension is achieved, affixing member 1 fits over base 3 within notches 9. There are ridges on the perimeter and inside edges of notches 9 (not shown) that interdigitate with ridges on the opposing edges of affixing member 1 (not shown) so that the graft can be incrementally compressed.

The various embodiments of the invention generally function in a similar manner, with some differences from one to another. In general, most embodiments function as follows: The device's hollow sleeve fits into a bone tunnel, and the attached base rests on the bone surface around the perimeter of the bone tunnel. Soft tissue (e.g., a tendon graft) passes through the sleeve, exiting through a notch in the sleeve above the bone surface (or other tissue surface). The soft tissue (or a suture attached to the soft tissue) is wrapped around or otherwise attached to one or more pegs on the surface of the disk (or affixing member). The graft is tensioned by rotating the disc (or affixing member). At each level of tension adjustment, the stability of any area of interest, including that of approximated surfaces, may be tested without compromising the established tension. By testing incremental changes in the stably-maintained tension, optimum conditions can be selected with greater confidence. The tissue is then affixed and compressed by apposition of the affixing device with the base. Tissues of various sizes, density, and quality can be accommodated.

In general, the surgeon directly supplies most of the tension as the tissue graft is pulled through the bone tunnel and sleeve. Wrapping the tissue graft around the sleeve is then used for fine, incremental adjustments to the tension. Normally, it will be convenient to turn the graft through no more than a rotation of about 360° or slightly less. More than 360° would result in excess friction and stress on the portion of the graft extending from the sleeve, and in most circumstances is not recommended. One rotation of about 360° or less should more than suffice to fine-tune the tension in most circumstances. If more tension is needed than can be provided by a single 360° rotation, then it will generally be preferred to start over rather than to continue turning the rotating portion of the device past 360°.

The sleeve remains in position, without rotating, as the graft is wrapped around it. Interdigitating teeth (or similar features) between the cap and the base allow only one-way rotation as the tension is increased to the desired point. Fixation of the graft is achieved by compressing it between the cap and the base. Structures on the cap and base, for example ledges, teeth, threads, or the like, inhibit backward rotations and loss of tension.

Where a particular tissue fixation does not involve a bone tunnel, the portion of the sleeve that would otherwise extend into the bone tunnel may be omitted.

The affixing device may optionally be attached to the base with a hinge. (However, a preferred embodiment does not include a hinge.)

The teeth and pegs on the rotating disc (or affixing member) and the base member can be arranged in various configurations, for example the teeth may lie on the central sleeve and the pegs on the inner surface of the disc, or vice versa. Various interdigitating shapes for the teeth and pegs may be used, not only the particular shapes depicted in the figures.

The device may optionally include flanges on the surface of the base lying next to the bone or other tissue, to assist stabilization using sutures, wires, screws, staples, or other affixing mechanisms.

The outer surface of the bone sleeve optionally includes a series of threads for integration into the bone, using otherwise standard tapping procedures. Alternatively, the threads may be self-tapping or self-locking. Preferably, the device and the pitch of the threads are configured to allow about two full turns before the bottom surface of the base is flush with the bone to facilitate interdigitation of threads on the column with the full thickness of cortical bone. Preferably, the threads on the bone sleeve include small "teeth" to inhibit "backing out" or "unwinding."

The central portion of the sleeve that extends above the bone may be used to enhance the tensioning function of the device (whether two- or three-piece). That is, the central "sleeve" acts as an axis about which torque or tension may be applied.

The "gear" or "tooth" interface between the base member and the affixing member allows incremental tensioning. The position of that interface can be outside the base, inside the base, on the lower surface of the sleeve, or on the upper surface of the sleeve.

The central column around which the graft is wrapped preferably provides friction to distribute force along a length of the graft, to reduce tension at the point where the graft is compressed between the affixing member and the base, and to reduce stress at the point where the graft exits the opening in the central column. The use of the central column in this manner, together with a relatively large interface between the graft and the surface of the device, significantly improves the security of the fixation, and reduces the likelihood of transection of the graft or other damage that might be caused by the device itself.

Figure 2A:
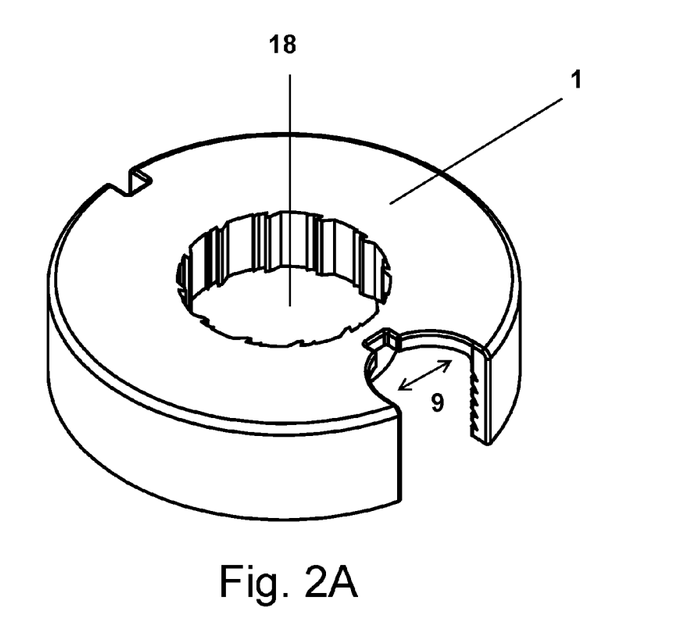
FIGS. 2A-F depict a two-component embodiment of the invention.
Figure 2B:
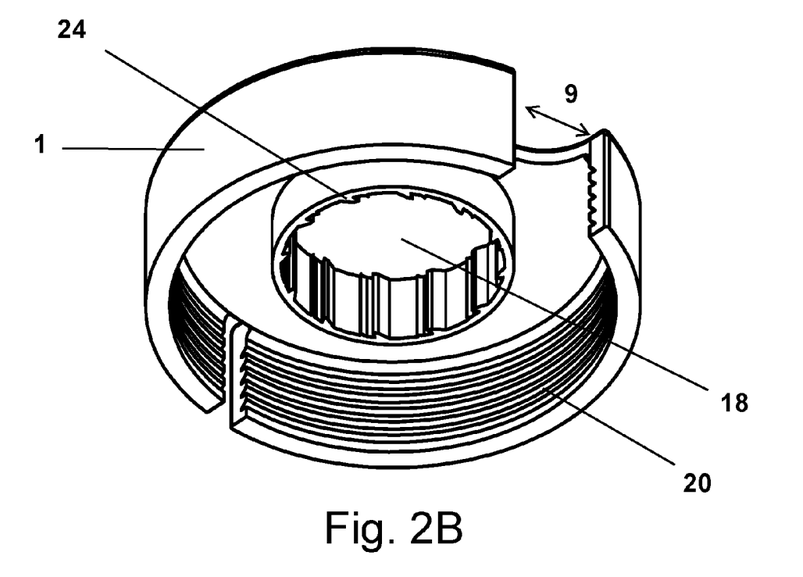
Figure 2C:
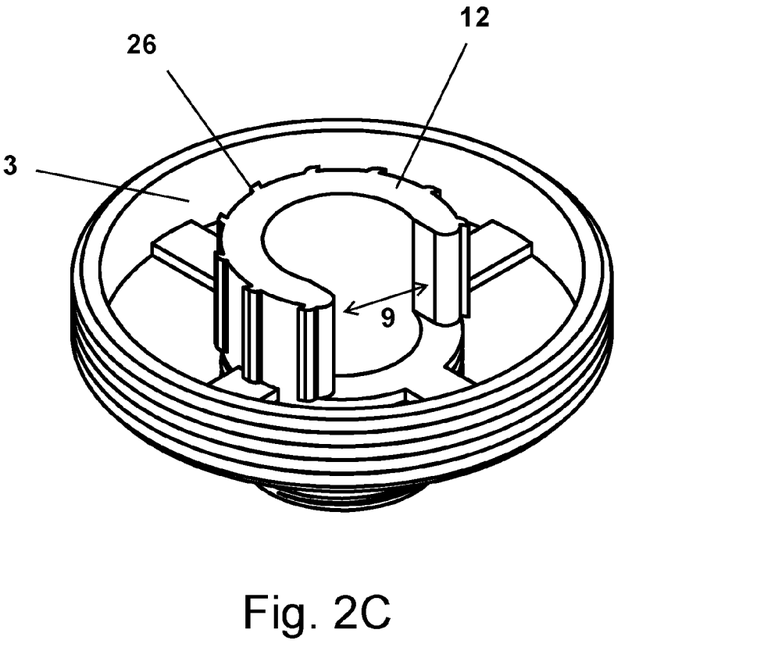
Figure 2D:
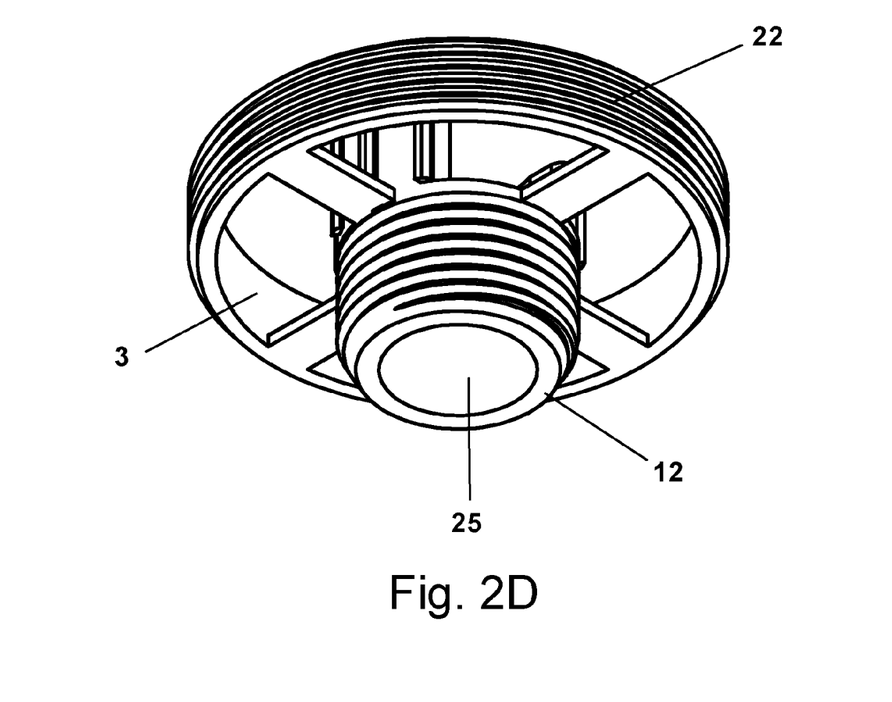

It is preferred that there be only one opening for the graft to exit the central column, as depicted for example in FIGS. 2A and 2B, rather than two openings as depicted for example in FIG. 1B. The opening(s) from the central column are preferably smooth and curved to facilitate motion of the graft from the bone tunnel, and to minimize potential damage to the graft at the point of exit through the opening.

When the device is used, for example, to secure a graft to a bone surface, a bone tunnel for graft passage is first tapped to create thread impressions. The sleeve from the base is advanced into the bone tunnel until tight. The tissue graft is passed through the bone tunnel and the hollow column of the base. The graft is passed through the opening (or one of the openings in the column). The graft is aligned with the opening(s) so that it is not crushed or damaged when the cap (or affixing member) is attached to the base. The cap (or affixing member) is positioned so that teeth in the center of the cap and teeth at the top of the base interdigitate. In some embodiments, the graft is attached to a small hook or knob on the outer rim of the cap. In other embodiments, the graft is simply gripped along with the affixing member using forceps or other surgical tool. The cap is rotated to tension the graft around the central column of the base. Once the desired tension is reached, the cap is compressed until the corresponding portions of the base and cap snap into place.

Optionally, elements such as the affixing member, the cap, and the rotating disc, may have holes or notches to permit the insertion of forceps for manipulation of the device. These features are preferably configured to allow manipulation using standard surgical instruments such as standard forceps, without the need for any atypical or special instruments. Alternatively, no special holes or notches are provided for forceps, and the forceps simply holds both the soft tissue and the affixing member (or cap) as the affixing member (or cap) turns, causing the soft tissue to wrap around the central column and increasing the tension.

Various optional or alternative features may be incorporated into the device, for example: A peg on the side of the affixing member or cap may be used for attaching grafts or sutures for tensioning. Horizontal ridges and vertical ridges on the base can be used to interdigitate with corresponding ledges or teeth on the inner surface of the affixing member or cap. These components support incremental graft tensioning (via the ridges) followed by incremental compression (with the ledges), to compress and fix the tissue in place. An opening may be provided in the affixing member, cap, or base to allow passage of the graft tissue. Locking threads may be placed on the bone sleeve to help lock the device into the bone tunnel. The device may comprise either two or three pieces overall. The embodiment depicted in FIG. 1A-C comprises three pieces, while the embodiments depicted in FIGS. 2A-F and FIGS. 3A-F comprise two pieces.

Alternative embodiments of the invention are depicted in FIGS. 2A-F and FIGS. 3A-F. The same reference numeral appearing in different figures should be understood to refer to corresponding or analogous components in the different embodiments, although the shapes and sizes may sometimes vary from one embodiment to another.

Figure 2E:
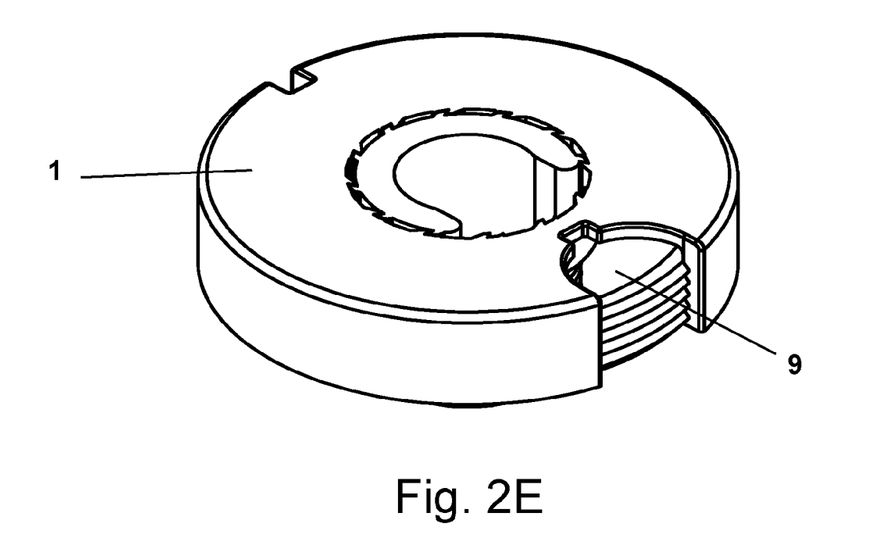
Figure 2F:
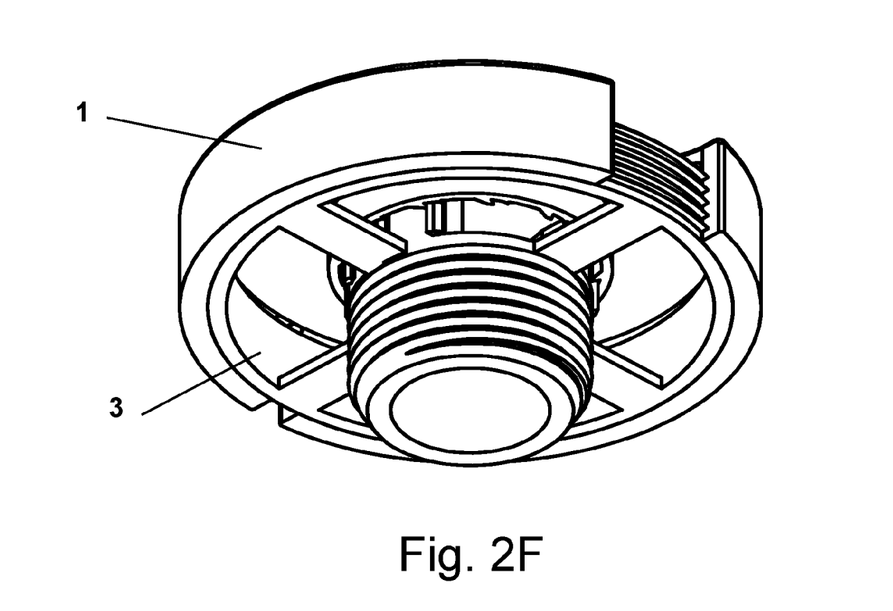
Figure 3A:
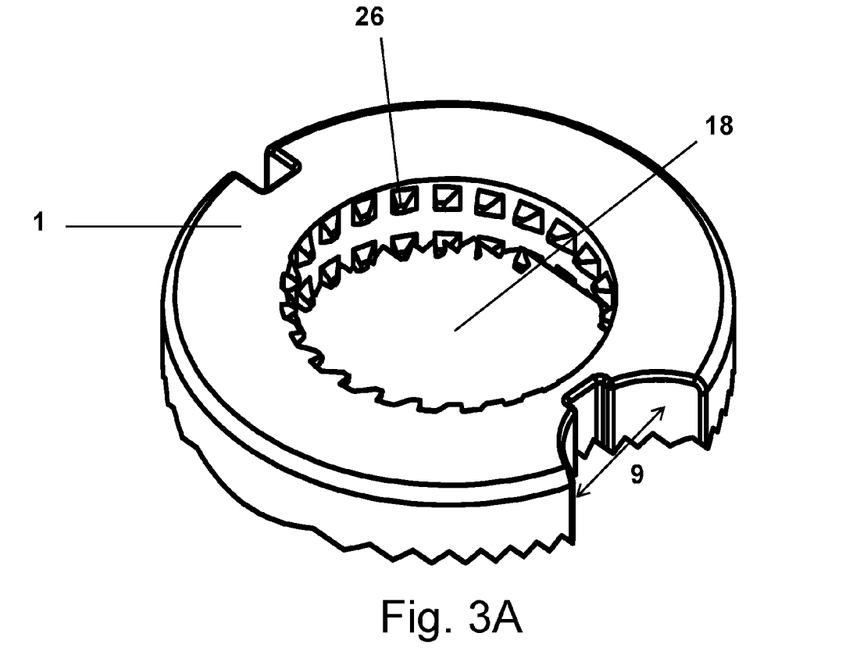
FIGS. 3A-F depict a different two-component embodiment of the invention.
Figure 3B:
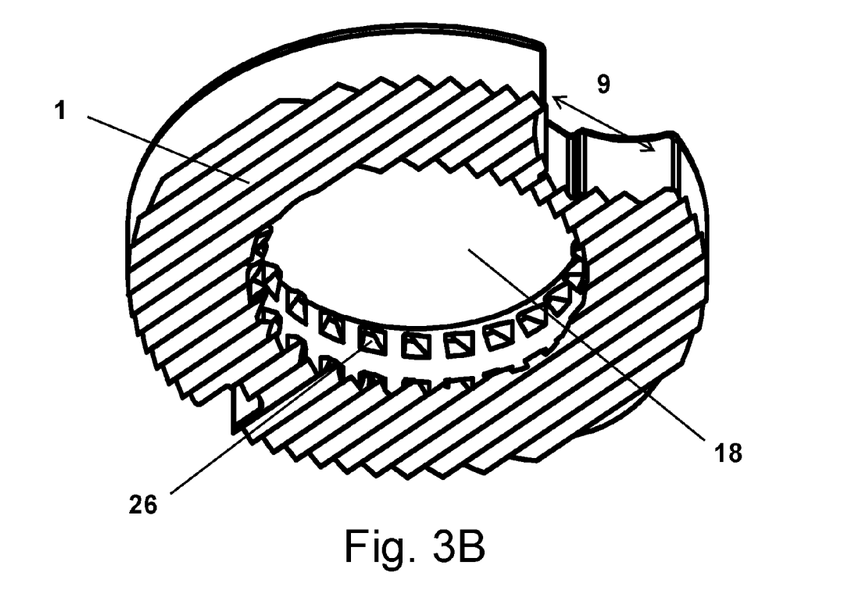
Figure 3C:
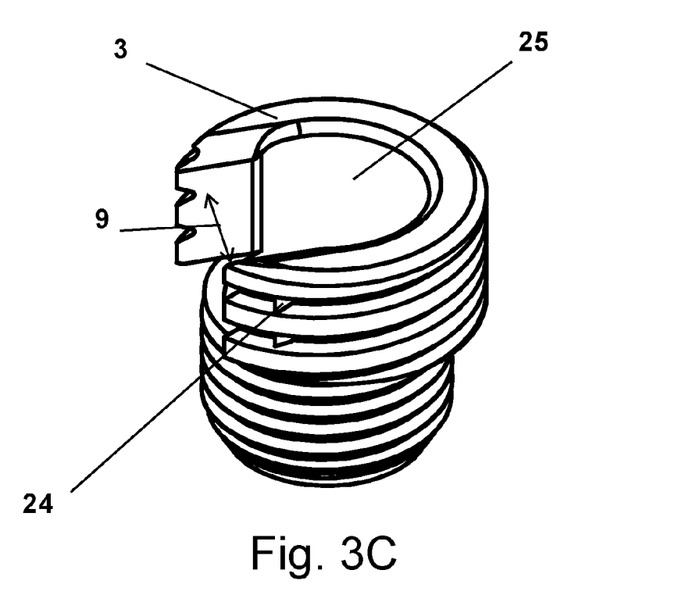
Figure 3D:
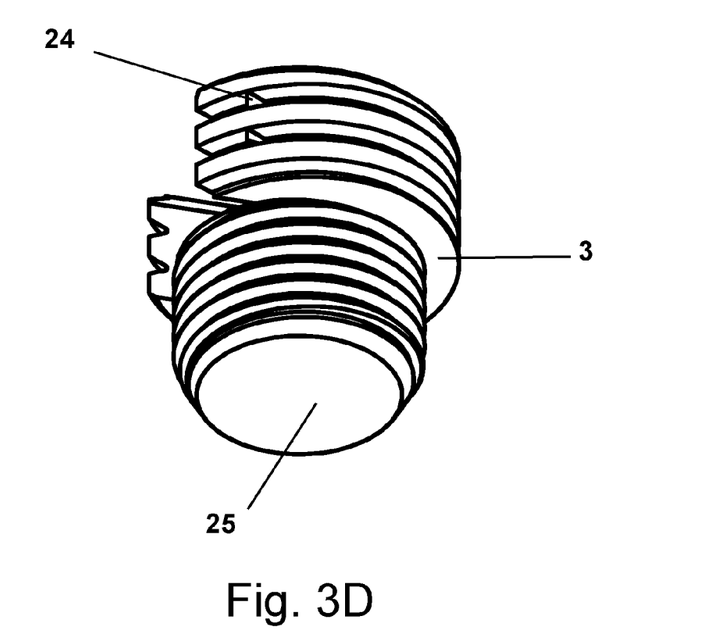
Figure 3E:
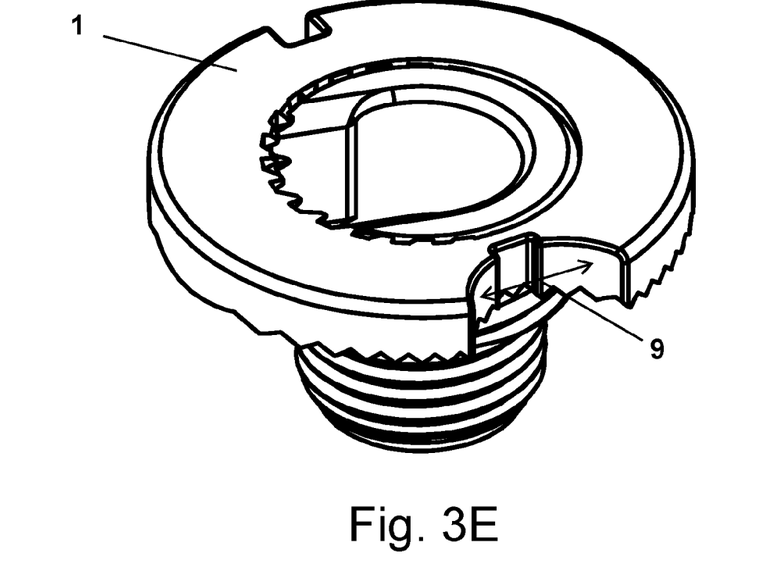
Figure 3F:
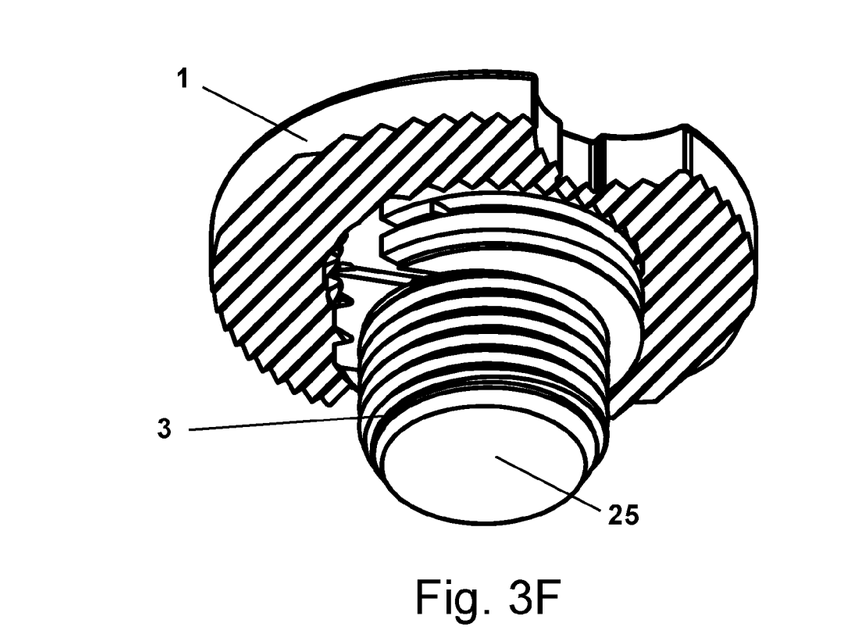

In the alternative embodiment depicted in FIGS. 2A-F (an embodiment sometimes called "GrabTen™ V1"), the lower threaded portion of sleeve 12 is secured in a bone tunnel, for example a tibial bone tunnel. The tendon graft is passed through the central portion 25 of sleeve 12. The surgeon initially tensions the graft simply by pulling it through sleeve 12 with forceps. Cap 1 is initially positioned above base 3 in the open position, and the graft is passed through opening 25 in sleeve 12 and openings 9 in base 3 and cap 1. Opening 9 in cap 1 should be over opening 9 in sleeve 12 on base 3. In the open position, lower ledge 20 of cap 1 interdigitates with upper ledge 22 on base 3. The ledges on base 3 and cap 1 are preferably ledges (without a pitch) rather than threads (with a pitch), so that cap 1 may turn freely about base 3. The graft and cap 1 are gripped with forceps, and cap 1 is turned to incrementally tension the graft as the graft wraps around sleeve 12. Teeth 24 on cap 1, on the circumference of opening 18, and teeth 26 on sleeve 12 cause the device to act as a ratchet-and-pawl, allowing rotation in one direction only. Cap 1 should be turned through no more than about 330 degrees (about 6 radians) to adjust the tension. If additional tension is desired, rather than continue turning, it is preferred to remove cap 1, unwind the graft from sleeve 12 (without releasing tension), and re-start the process. Depending on the dimensions of the specific device, the process typically allows up to about 2 cm of fine tensioning, which should suffice in most circumstances. Once the tensioning process is completed, the surgeon may either: (1) Release the graft from the forceps and continue turning cap 1. The graft "tail" will then be wound around sleeve 12 and contained within the device, without applying additional tension; or (2) Cut off any portion of the graft remaining outside the cap. Finally, cap 1 is snapped closed over the graft to compress it and fix it in place, as shown in FIGS. 2E and 2F. The ledges 20 of cap 1 and the ledges 22 of base 3 interdigitate to hold cap 1 and the graft in place, compressing and affixing the graft.

In the alternative embodiment depicted in FIGS. 3A-F (an embodiment sometimes called "GrabTen™ V2"), the lower threaded portion of base 3 is secured in a bone tunnel, for example a tibial bone tunnel. The tendon graft is passed through the central opening 25 in base 3. The graft is tensioned by pulling; the cap 1 is initially positioned in the open position, and the graft is passed through openings 9 in base 3 and cap 1, with opening 9 in cap 1 over opening 9 in base 3, similarly to what is described above for the V1 embodiment. The graft is gripped along with the affixing member using forceps or other surgical tool. Cap 1 is turned to incrementally tension the graft around base 3. There are threads with teeth 24 and 26 on base 3 and in cap 1, respectively. As cap 1 turns, it slowly advances down base 3 because of the pitched threads on both components. The teeth 24 and 26 on the threads of base 3 and cap 1 inhibit cap 1 from turning in the reverse direction and releasing tension. Once the tensioning process is completed, the surgeon may either: (1) Release the graft from the forceps and continue turning cap 1. The graft "tail" will then be wound around base 3, and contained within the device without applying additional tension; or (2) Cut off any portion of the graft remaining outside cap 1. Finally, cap 1 is turned further to compress the graft and fix it in place. In the "closed" position, the lower surface of cap 1 is typically about 1-2 mm above the bone surface. Tensioning is achieved on the first turn of cap 1 about base 3, and compression is achieved on the second turn. The "V2" embodiment is preferably designed for cap 1 to undergo two full turns as described. If insufficient tension is achieved in the first turn, the graft can be unwound and the process begun anew. The device is intended primarily for fine tension adjustments, with the gross tension applied directly by the surgeon in pulling the graft through the bone tunnel and column.

The novel GrabTen™ device has various uses including, for example: Anterior/Posterior Cruciate Ligament Reconstruction, Meniscal Repair, Rotator Cuff Repair, Shoulder Labrum Repair, and Biceps Tenodesis. The dimensions of the device may be customized for the intended use, the size of the patient, and the species of the patient. The device may be used in humans, dogs, cats, horses, and other vertebrates. Optionally, the device may be fabricated from bioabsorbable materials.

In an alternative embodiment, the perimeter of the affixing member and the shape of the depression within the base may have, rather than a circular shape, instead a regular polygonal shape (e.g., a square, a regular hexagon, a regular octagon, etc.) such that the polygonal outline of the affixing member fits snugly into the polygonal depression of the base. The corners and overall fit of these polygonal shapes to one another take the place of catches, ridges, teeth, gears, etc. for incremental tensioning of the graft. Tension is held by rotating the affixing member from one complementary position to the next—e.g., by rotating 90° in the case of a square, by rotating 60° in the case of a hexagon, by rotating 45° in the case of an octagon, etc. The overall function in this alternative embodiment is otherwise essentially similar. Incremental advancement of the tension is still secured by interdigitation between the base and the affixing member, but in this embodiment the interdigitation results from the shapes of the components themselves, rather than from specific surface modifications such as steps, wedges, gears, or pegs.

More generally, in this alternative embodiment the shape need not even be that of a regular polygon, but can more broadly be any shape that has a rotational symmetry, and that will produce a snug fit between the affixing member and the base when the two are pressed together, so that the affixing member will not readily slip out of place. For example, the shape may be an ellipse, a rectangle, a star (e.g., a star having 5, 6, 7, 8, or more points), a trefoil, a pentafoil, a hexafoil, an octafoil, etc.

Prototype Testing.

Prototypes of the novel device with dimensions adapted for use in ACL reconstruction will be fabricated from medical grade poly-L-lactic acid. Mechanical testing will first be conducted in an established animal model for human implants (limbs from young bovine cadavers), followed by testing in live animals, followed by testing in live humans—all in accordance with applicable laws and regulations.

Sixteen stifles (mid-femur to tarsus) collected from young bovines euthanized for reasons unrelated to this study will be wrapped in saline soaked towels, double wrapped in sealed plastic bags, and frozen at −20° C. until graft collection and fixation. Prior to graft collection, limbs will be randomly assigned to one of two treatment groups: (1) an embodiment of the novel GrabTen™ device, or (2) and conventional screw and washer. Hamstring grafts will be collected and prepared. Briefly: The insertion of the semitendinosus and gracilis muscles will be dissected free of their muscular origins. Without disturbing the tendinous insertions, attached dense connective tissue and fascia of the cranial tibialis will be elevated using a combination of blunt and sharp dissection to the distal third of the tibia, where the tissue will be sharply transected. Elevated tissues will be trimmed and twisted to give a final diameter of approximately 10 mm. The graft will be wrapped within a "Chinese finger trap" made of polyglactin 910.

Tibiae will be secured in a testing fixture attached to an Instron mechanical testing system. One end of each graft will be held in a cryogrip attached to a load cell with sufficient length to be fixed to the tibia. Following otherwise standard procedures, grafts will be placed in the bone tunnel and secured with either a GrabTen™ device or a conventional screw and washer. Tension will be measured during the process, and also continuing for five minutes after graft fixation. Grafts will be tested to failure in a single cycle under axial load applied along the physiologic axis of the graft. Stiffness, yield, and failure loads and energies will be determined.

Biomechanical tests will include, among others: single cycle to failure testing, fatigue testing, quantification of incremental tension application, and creep testing. Device embodiments will be compared to one another as well as to commercially available devices. Standard preclinical testing will be performed in accepted models with appropriately sized devices to establish safety and efficacy. Clinical trials will be performed in accordance with applicable laws and regulations.

Statistical Analysis.

Due to the nested factorial design of the study, parametric response variables will be treated as being continuous, and will be tested for normality using Shapiro-Wilk statistics, with the null hypothesis rejected at $p \leq 0.05$. Non-normal data will be transformed. Multivariate analyses of variance will be conducted to evaluate fixed effects of the graft fixation on the collinear response variables. The random variance of limb nested within cohort will be used as the error term for effect of graft fixation. Statistical significance will be assessed at $p \leq 0.05$.

Expected Results:

(1) That hamstring ACL reconstruction grafts fixed with a GrabTen™ implant will have more consistent and stable tensioning behavior than those fixed with other devices designed for the same purpose, such as those employing screw and washer. (2) That hamstring ACL reconstruction grafts fixed with a GrabTen™ implant will have superior mechanical properties compared to those fixed with with other devices designed for the same purpose, such as those employing screw and washer.

Notes Concerning Nomenclature and Certain Alternative Embodiments

The specification and claims sometimes use the terms "graft," "graft tissue," and "soft tissue" interchangeably. In some contexts, the word "graft" refers to tissue harvested from some different location, while "soft tissue" carries no such connotation—and frequently the latter term would be used where a tendon or ligament were to be reattached in the same location. For purposes of describing the present invention and its uses, however, it generally will not matter whether a tissue is a true "graft" or a tissue reattached in the same location. Accordingly, these distinctions—which may be important in other contexts—should not be given undue weight when reading the present specification and claims, unless context clearly indicates otherwise. The present invention will work with both "graft tissue" harvested from a different location, and soft tissue reattached in the same location. Also, it may be used in conjunction with a suture or synthetic material that is in turn attached to a soft tissue. The most common applications of the invention are expected to be in attaching or re-attaching tendons and ligaments, but the invention may also be used to attach other types of tissue as well—e.g., in skin grafts, or in supports for a bladder sling. The attachment will generally be made to a bone, but in some cases can be made to the surface of another soft tissue. All the above are considered to be within the scope of the present invention, regardless of the particular nomenclature used in a particular location.

The complete disclosures of all cited references are hereby incorporated by reference, including the complete disclosure of priority application 62/145,552. In the event of an otherwise irreconcilable conflict, however, the present specification shall control.

What is claimed:

1. A device adapted to affix a soft tissue or a suture attached to a soft tissue to a bone surface or other tissue surface; said device comprising a base and an affixing member, wherein:
   (a) said base comprises:
      (i) a top surface and a bottom surface;
      (ii) a passageway extending through said bottom surface and through said top surface, wherein said passageway comprises smooth sides through which a soft tissue or a suture attached to a soft tissue may pass, and
      (iii) at least one opening in said top surface extending from said passageway, wherein each said opening has one or more smooth edges over which a soft tissue or a suture attached to a soft tissue may pass;
   wherein:
      (iv) the perimeter of said base has a generally circular shape;
   (b) said affixing member is adapted to fit securely around or inside the generally circular perimeter of said base; wherein said affixing member also has an opening through which the soft tissue or a suture attached to the soft tissue may pass to or from the passageway through said base;
   (c) a plurality of securing elements contained on the perimeter of said base, or contained on said affixing member, or both; wherein said securing elements are adapted to hold said affixing member securely in any one of a plurality of positions as selected by a surgeon, while said affixing member remains securely attached to a soft tissue or to a suture attached to a soft tissue, and wherein said affixing member thereby applies a stable tension to the soft tissue; and wherein said securing elements are adapted to permit the surgeon readily to alter the selected position, thereby allowing the surgeon to alter the stable tension applied to the soft tissue during surgery, and allowing the surgeon to choose a position that stably applies the amount of tension selected by the surgeon; and to maintain the chosen position, and thereby maintain the selected amount of tension on the soft tissue following surgery as the soft tissue or a suture attached to the soft tissue is partially compressed between said affixing member and said base.

2. The device of claim 1, additionally comprising a tubular sleeve extending from said bottom surface of said base, wherein the exterior of said tubular sleeve is adapted for insertion into a bone tunnel; and wherein said passageway continues through said tubular sleeve.

3. The device of claim 2, wherein the exterior of said tubular sleeve comprises threads adapted to secure said tubular sleeve in a bone tunnel.

4. The device of claim 3, wherein the threads allow only unidirectional rotation, so that once the interface between said tubular sleeve and the bone is tightened, the tightening cannot readily be reversed without stripping the threads.

5. The device of claim 1, wherein said device is bioabsorbable.

6. The device of claim 1, additionally comprising at least one anchor adapted to secure said base to the bone or other tissue surface and to impart stability for said base member to resist one or more of: rotational movement, axial movement, and translational movement.

7. The device of claim 6, wherein said at least one anchor comprises at least one spike adapted to be driven into bone.

8. The device of claim 1, wherein said device is adapted to have a profile that does not protrude above surrounding soft tissues when said device is surgically implanted under the skin of a patient.

9. The device of claim 1, wherein said securing elements comprise a plurality of teeth on said base, and a plurality of teeth on said affixing member, wherein the said teeth on said base and said teeth on said affixing member are configured to engage with one another, and to allow rotation of said affixing member about said passageway in one direction only, so that the tension on the soft tissue may be incrementally and stably adjusted.

10. The device of claim 1, wherein said affixing member and said base are adapted to be affixed to one another in any one of multiple configurations as selected by a surgeon, wherein the multiple configurations apply different levels of compression to the soft tissue.

11. The device of claim 1, wherein said affixing member additionally comprises at least one feature adapted to securely attach to a soft tissue or to a suture attached to a soft tissue.

* * * * *